United States Patent [19]

Deger et al.

[11] Patent Number: 5,510,377

[45] Date of Patent: Apr. 23, 1996

[54] STERILANT GAS MIXTURE COMPRISING ALKYLENE OXIDE AND 1,1,1,2,3,3,3-HEPTAFLUOROPROPANE

[75] Inventors: Hans-Matthias Deger, Hofheim-Wallau; Rainer Henrici, Neu-Anspach; Ewald Preisegger, Nauheim, all of Germany

[73] Assignee: Hoechst AG, Frankfurt am Main, Germany

[21] Appl. No.: 371,478

[22] Filed: Jan. 11, 1995

Related U.S. Application Data

[63] Continuation of Ser. No. 43,353, Apr. 6, 1993, abandoned.

[30] Foreign Application Priority Data

Apr. 21, 1992 [DE] Germany ................. 42 13 091.3

[51] Int. Cl.$^6$ .................... A01N 43/20; A01N 25/18
[52] U.S. Cl. ........................... 514/475; 422/34
[58] Field of Search ...................... 514/475; 422/34

[56] References Cited

U.S. PATENT DOCUMENTS

| | | | |
|---|---|---|---|
| 2,037,439 | 4/1936 | Schrader et al. ............. | 167/39 |
| 2,891,838 | 6/1959 | Kaye ........................... | 21/58 |
| 4,971,716 | 11/1990 | Batt et al. .................... | 252/171 |
| 5,039,485 | 8/1991 | Conviser et al. ............. | 422/34 |
| 5,084,190 | 1/1992 | Fernandez ................... | 252/8 |
| 5,124,053 | 6/1992 | Iikubo et al. ................ | 252/8 |
| 5,254,309 | 10/1993 | Felix et al. .................. | 422/34 |

OTHER PUBLICATIONS

Derwent Database, Abstract # 91-159429 (JP-A-3 093 890), 1991.

*Primary Examiner*—S. Mark Clardy
*Attorney, Agent, or Firm*—Connolly & Hutz

[57] ABSTRACT

A sterilant gas mixture is presented for cold-gas sterilization, which comprises alkene oxide and 1,1,1,2,3,3,3-heptafluoropropane.

The sterilant gas mixture comprises from 12 to 22 mol % of ethylene oxide or propylene oxide and from 78 to 88 mol % of 1,1,1,2,3,3,3-heptafluoropropane.

6 Claims, 1 Drawing Sheet

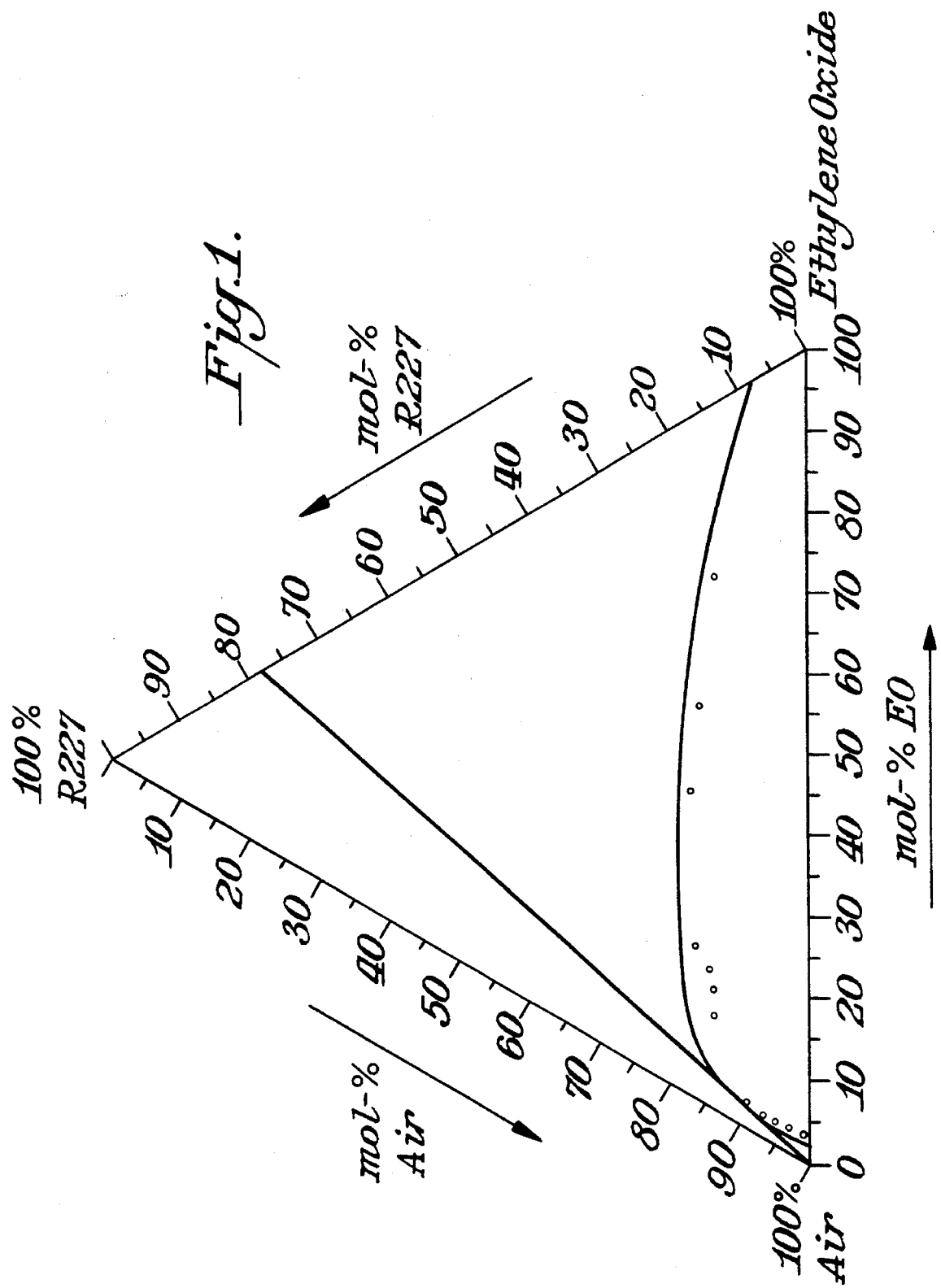

STERILANT GAS MIXTURE COMPRISING ALKYLENE OXIDE AND 1,1,1,2,3,3,3-HEPTAFLUOROPROPANE

This application is a continuation of application Ser. No. 08/043,353 filed on Apr. 6, 1993 abandoned.

The present invention relates to a sterilant gas mixture for cold-gas sterilization.

Sterilization is to be understood as the killing or the inactivation of insects, bacteria, viruses, fungi and other microorganisms. The killed or inactivated organisms are not removed in this sterilization.

Sterilization conventionally employed in industry, using boiling water, hot steam or hot air, is not generally applicable. In certain fields of medicine, equipment, systems and tools have to be sterilized which are either sensitive to moisture or which cannot withstand the temperatures, from 100° to 180° C., of a hot-gas sterilization.

In these cases, a cold-gas sterilization is carried out in which ethylene oxide and propylene oxide are used as the sterilant gas. These alkene oxides are highly efficient sterilizing media which deploy their full activity even at low temperatures. The objects to be sterilized are not thermally stressed during cold-gas sterilization, and the alkene oxides, upon completion of the sterilization process, can be quickly removed from the sterilized article as they are highly volatile. Although ethylene oxide and propylene oxide could be used on their own for sterilization, it is more common, because of the risk of forming ignitable mixtures with air, to use them in a mixture with a desensitizing gas. A known desensitizing gas for sterilant gas mixtures on the basis of ethylene oxide is carbon dioxide. In order to prevent the formation of ignitable mixtures with air, desensitization with $CO_2$ only permits the use of at most 7 mol % of ethylene oxide as sterilant gas mixture.

It is therefore necessary to carry out the sterilization either at higher pressures or to use longer contact times. Furthermore, because of the large difference in vapor pressure between $CO_2$ and ethylene oxide, it is possible that the sterilant gas mixture drawn from the liquid phase of a storage tank may be enriched with ethylene oxide as the vapor phase in the reservoir increases and the liquid phase therein decreases, as a result of which there is a risk of ignitable mixtures with air being formed.

Consequently it has been proposed to add dichlorodifluoromethane (R12) as the desensitizing gas to the sterilant gas mixture based on ethylene oxide.

Because of the fluorochlorohydrocarbon/ozone issue, it is no longer permitted to use dichlorodifluoromethane (R12) for this purpose.

The object of the invention is therefore to provide a sterilant gas mixture for cold-gas sterilization, which contains no dichlorodifluoromethane (R12), does not form an ignitable mixture with air, and permits sterilization in a short time without the application of hyperatmospheric pressure or elevated temperatures. The sterilant gas mixture according to the invention for cold-gas sterilization comprises alkene oxide and 1,1,1,2,3,3,3-heptafluoropropane (R227).

The sterilant gas mixture according to the invention optionally comprises a) from 12 to 22 mol % of ethylene oxide and from 78 to 88 mol % of 1,1,1,2,3,3,3-heptafluoropropane (R227) or b) from 12 to 22 mol % of propylene oxide and from 78 to 88 mol % of 1,1,1,2,3,3,3-heptafluoropropane (R227).

The sterilant gas mixture according to the invention may also optionally be modified in that c) the alkene oxide is a mixture of ethylene oxide and propylene oxide;

d) the mixture contains inert gases in amounts of up to 20 volume %;

e) the inert gas is nitrogen, carbon dioxide or a noble gas.

A further advantage of the sterilant gas mixture according to the invention comprising 1,1,1,2,3,3,3-heptafluoropropane (R227) as the desensitizing agent stems from the fact that, particularly in the case of sterilant gas mixtures based on ethylene oxide, the boiling point difference is distinctly smaller. This reduces the risk of the concentration shifting in the direction of ethylene oxide enrichment as the reservoir becomes progressively emptier. Ethylene oxide boils at 10.7° C. The boiling point of dichlorodifluoromethane (R12) is at −29.8° C.; that of 1,1,1,2,3,3,3-heptafluoropropane (R227) is at −17.4° C. This means that smaller concentration shifts will arise in the sterilant gas mixture according to the invention than in the previously used mixture of ethylene oxide and R12.

In the sterilant gas mixture based on an ethylene oxide/propylene oxide mixture with R227, the boiling point of R227 (−17.4° C.) is more favorable than that of R12 (−29.8° C.), because the boiling point of R227 (−17.4° C.) is closer both to the boiling points of ethylene oxide (10.7° C.) and propylene oxide (35° C.) and to the boiling point range of the ethylene oxide/propylene oxide mixture. The partial pressure of propylene oxide in the ethylene oxide/propylene oxide mixture is in a range at which the ethylene oxide/propylene oxide mixture can be drawn from the reservoir without additional heating, which is not always the case if propylene oxide on its own is used in the sterilant gas mixture. If the total pressure of the sterilant gas mixture according to the invention in the liquid phase at a given temperature should be too small, the pressure in the reservoir can be increased by adding inert gas, without serious consequences regarding the formation of ignitable mixtures with air.

The sterilant gas mixture according to the invention can be used to sterilize a large variety of different articles. Examples from the field of medical equipment and materials are endoscopes, plastic articles such as elastomeric seals in medical apparatuses, piping, incubators, pacemakers, rubber products such as tubes, gloves, catheters, instruments such as injection needles, scalpels and many more. Examples of application outside the medical field are the sterilization of furs, paper products, transport containers or freight holds of aeroplanes, trains and ships.

The sterilant gas mixture according to the invention is active against insects, bacteria, viruses, fungi and many other microorganisms.

The sterilant gas mixture according to the invention can be prepared by known mixing techniques which are familiar to the person skilled in the art working in this field. For example, it is possible to pump each component of the sterilant gas mixture separately into a reservoir, and the mixing ratio can be set by weighing the reservoir or by measuring the volume flow of each individual component. Mixing the individual components can be carried out in the reservoir by recirculation until a homogeneous mixture has been achieved. The accurate setting of the mixing ratio can subsequently be checked by an analytical procedure.

The reservoirs which can be used for the sterilant gas mixture according to the invention include those previously used for mixtures of ethylene oxide and R12.

The determination of the ignition limits of the sterilant gas mixture according to the invention was carried out in an apparatus according to DIN 51 649 (Part 1). Different concentrations of the gas mixture were formed using a Wösthoff gas-mixing pump, and air was introduced using a mass flow rate meter supplied by Brooks. The temperature in the ignition vessel was 65° C.; the experiments were carried out at atmospheric pressure. The results of the ignition limit determination of the ternary system alkylene oxide/R227/air were plotted as graphs in the triangular diagram (FIG. 1). Plotted in FIG. 1 are the individual values and a regression curve. This regression curve shows the concentration dependence of the ignition limits for alkylene oxide/R227/air mixtures.

In addition, a straight line is drawn in FIG. 1, whose origin is in the bottom left hand corner (100 mol % air) and which is a tangent of the regression curve. This straight line in FIG. 1 intersects the axis which indicates the molar fraction of R227. This intersection indicates the ratio at which ignitable mixtures of alkylene oxide and R227 just cease to be formed in a mixture with air. The 78 mol % of R227 results in 22 mol % of alkylene oxide, being the difference to 100 mol %. Mixtures containing less than 22 mol % of alkylene oxide do not form ignitable mixtures with air, if the alkylene oxide is mixed with R227 as desensitizing agent.

As comparative experiments using 1,2,2,2-tetrafluoroethane (R134a) as the desensitizing component have shown, the ignition limit of such a sterilant gas mixture is reached from an ethylene oxide content as low as 14 mol %. Desensitization of ethylene oxide using R134a is therefore considerably less effective than that using R227.

We claim:

1. A sterilant gas mixture for cold-gas sterilization, comprising a mixture of from 12 to 22 mol % of alkene oxide and from 78 to 88 mol % of 1,1,1,2,3,3,3-heptafluoropropane, said alkene oxide being selected from the group consisting of ethylene oxide and propylene oxide or mixtures thereof.

2. The sterilant gas mixture as claimed in claim 1, additionally comprising inert gas in amounts of up to 20 volume %.

3. The sterilant gas mixture as claimed in claim 2, wherein the inert gas is nitrogen, carbon dioxide or noble gas.

4. A sterilant gas mixture for cold-gas sterilization, comprising a mixture of from 12 to 22 mol % of alkene oxide and from 78 to 88 mol % of 1,1,1,2,3,3,3-heptafluoropropane, said alkene oxide being selected from the group consisting of ethylene oxide and propylene oxide or mixtures thereof, said mixture further comprising inert gas in amounts of up to 20 volume %.

5. The sterilant gas mixture as claimed in claim 4, wherein the inert gas is nitrogen, carbon dioxide or noble gas.

6. A sterilant gas mixture for cold-gas sterilization, comprising a mixture of from 12 to 22 mol % of alkene oxide and from 78 to 88 mol % of 1,1,1,2,3,3,3-heptafluoropropane, said alkene oxide being selected from the group consisting of ethylene oxide and propylene oxide or mixtures thereof, said mixture further comprising inert gas selected from the group of nitrogen, carbon dioxide or noble gas in amounts of up to 20 volume %.

* * * * *